United States Patent
Watanabe et al.

(10) Patent No.: US 10,703,646 B2
(45) Date of Patent: Jul. 7, 2020

(54) FLUID STERILIZATION DEVICE

(71) Applicant: NIKKISO CO., LTD., Tokyo (JP)

(72) Inventors: Shinya Watanabe, Ishikawa (JP); Nobuhiro Torii, Ishikawa (JP)

(73) Assignee: NIKKISO CO., LTD., Tokyo (JP)

( * ) Notice: Subject to any disclaimer, the term of this patent is extended or adjusted under 35 U.S.C. 154(b) by 45 days.

(21) Appl. No.: 16/012,615

(22) Filed: Jun. 19, 2018

(65) Prior Publication Data

US 2018/0370822 A1    Dec. 27, 2018

(30) Foreign Application Priority Data

Jun. 27, 2017   (JP) ................. 2017-125497

(51) Int. Cl.
*C02F 1/32* (2006.01)
*A61L 2/10* (2006.01)

(52) U.S. Cl.
CPC ............... *C02F 1/325* (2013.01); *A61L 2/10* (2013.01); *A61L 2202/11* (2013.01); *C02F 2201/003* (2013.01); *C02F 2201/3222* (2013.01); *C02F 2201/3225* (2013.01); *C02F 2201/3228* (2013.01); *C02F 2303/04* (2013.01)

(58) Field of Classification Search
None
See application file for complete search history.

(56) References Cited

U.S. PATENT DOCUMENTS

| 2015/0114912 A1* | 4/2015 | Taghipour | C02F 1/325 210/748.11 |
| 2015/0144575 A1* | 5/2015 | Hawkins, II | A61L 2/10 210/748.11 |
| 2016/0083272 A1* | 3/2016 | Rajagopalan | C02F 1/325 250/435 |

FOREIGN PATENT DOCUMENTS

JP    2014233712 A    12/2014

* cited by examiner

*Primary Examiner* — Kishor Mayekar
(74) *Attorney, Agent, or Firm* — Muncy, Geissler, Olds & Lowe, P.C.

(57) ABSTRACT

A fluid sterilization device includes: a housing formed with a processing passage for sterilizing a fluid passing through the processing passage; a light source that radiates ultraviolet toward the processing passage; and a transmissive member provided between the light source and the processing passage and transmitting the ultraviolet light radiated by the light source. The transmissive member is a one-piece component including: a focusing part that focuses the ultraviolet light radiated by the light source toward the processing passage by refracting or reflecting the ultraviolet light; an exit part that guides the ultraviolet light transmitted through the focusing part toward the processing passage, and a supported part formed on an outer circumference of the exit part to be contiguous with the exit part, and supported by the housing. The exit part is exposed to the processing passage.

9 Claims, 5 Drawing Sheets

FLUID STERILIZATION DEVICE

CROSS-REFERENCE TO RELATED APPLICATIONS

This application is based upon and claims the benefit of priority from the prior Japanese Patent Application No. 2017-125497, filed on Jun. 27, 2017, the entire contents of which are incorporated herein by reference.

BACKGROUND OF THE INVENTION

1. Field of the Invention

The present invention relates to a fluid sterilization device.

2. Description of the Related Art

It is known that ultraviolet light has sterilization capability. Devices that radiate ultraviolet light are used for sterilization in medical and food processing fronts. Devices that sterilize a fluid such as water continuously by irradiating the fluid with ultraviolet light are also used. One example is a device in which an ultraviolet LED is provided outside an end of a container formed by a straight pipe (see JP2014-233712 publication).

The device is provided with a collimating lens that refracts ultraviolet light radiated from the ultraviolet LED with a certain spread and transmitted through the collimating lens and turns the transmitted light into parallel light. The ultraviolet light radiated from the ultraviolet LED is refracted by the collimating lens and then transmitted through a glass plate to irradiate a space in the container.

However, the ultraviolet light radiated from the ultraviolet LED undergoes loss before reaching the interior of the container due to the reflection on the incidence surface and reflecting surface of the collimating lens and the reflection on the incidence surface of the glass plate.

SUMMARY OF THE INVENTION

In this background, one illustrative purpose of the present invention is to provide a novel technology capable for improving the efficiency of sterilizing a fluid with ultraviolet light radiated from a light source.

The fluid sterilization device according to an embodiment comprises: a housing formed with a processing passage for sterilizing a fluid passing through the processing passage; a light source that radiates ultraviolet toward the processing passage; and a transmissive member provided between the light source and the processing passage and transmitting the ultraviolet light radiated by the light source. The transmissive member is a one-piece component including: a focusing part that focuses the ultraviolet light radiated by the light source toward the processing passage by refracting or reflecting the ultraviolet light; an exit part that guides the ultraviolet light transmitted through the focusing part toward the processing passage, and a supported part formed on an outer circumference of the exit part to be contiguous with the exit part, and supported by the housing, wherein the exit part is exposed to the processing passage.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

Figure 1:
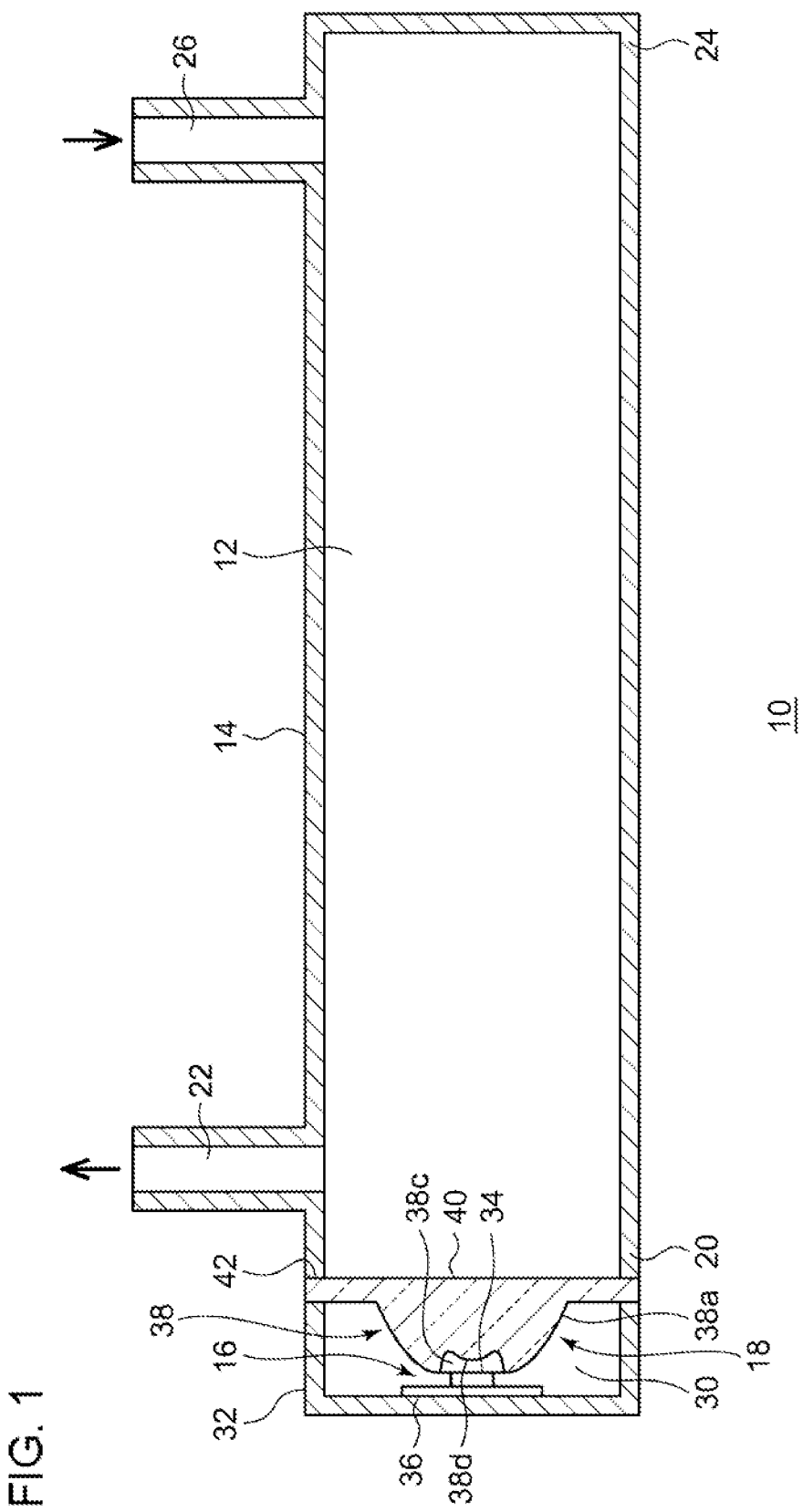
FIG. 1 is a cross-sectional view showing a schematic configuration of a fluid sterilization device according to the first embodiment.

A fluid sterilization device according to an embodiment of the present invention comprises: a housing formed with a processing passage for sterilizing a fluid passing through the processing passage; a light source that radiates ultraviolet toward the processing passage; and a transmissive member provided between the light source and the processing passage and transmitting the ultraviolet light radiated by the light source. The transmissive member is a one-piece component including: a focusing part that focuses the ultraviolet light radiated by the light source toward the processing passage by refracting or reflecting the ultraviolet light; an exit part that guides the ultraviolet light transmitted through the focusing part toward the processing passage, and a supported part formed on an outer circumference of the exit part to be contiguous with the exit part, and supported by the housing, wherein the exit part is exposed to the processing passage.

According to this embodiment, the ultraviolet light exiting the light source is directed by the focusing unit toward the processing passage so that the amount of ultraviolet light not contributing sterilization is reduced and the efficiency of sterilizing the fluid is improved. Since the transmissive member is configured as a one-piece component, reflection on the interface encountered by the ultraviolet radiated by the light source before reaching the processing passage is reduced. Since the exit part is exposed to the processing passage and is in contact with a highly refractive fluid in the processing passage, the refraction index difference at the interface of the exit part is reduced.

The surface of the exit part may be flat. Since the refractive index difference at the interface of the exit part is reduced, it is not necessary to work the surface from an optical perspective. This simplifies the shape of the transmissive member and reduces the manufacturing cost. The surface of the exit part forms the wall surface of the processing passage. Therefore, the flow of the liquid in the processing passage is not blocked seriously by configuring the surface to be flat.

The supported part may be a flange having a surface flush with the surface of the exit part. In this way, the transmissive member having a flange can be configured in a simple shape.

The transmissive member is a molded component. In this way, mechanical work can be omitted or reduced.

The transmissive member may be made of synthetic quartz. This reduces degradation of the transmissive member even when the light source radiating ultraviolet light is used.

The diameter D1 [mm] of the outer edge of the supported part of the transmissive member may be 1.5 times the maximum diameter D2 of the exit part or larger. This ensures that the transmissive member is supported by a large housing.

The housing may include a cylindrical flow passage tube that forms the processing passage. The outer diameter D3 [mm] of the flow passage tube may be larger than the maximum diameter D2 [mm] of the exit part. This ensures that most of the ultraviolet light exiting the exit part is radiated into the processing passage.

The outer diameter D3 [mm] of the flow passage tube may be smaller than the diameter D1 [mm] of the outer edge of the supported part. This ensures that the transmissive member is supported by a component provided on the outer circumference of the flow passage tube.

Given that the flow passage tube has an inner diameter D4 [mm] and a length L [mm], L/D4 may be 20 or less.

The housing may include: a first component that covers an outer circumferential surface near an opening at one end of the flow passage tube; and a second component that covers the opening of the one end of the flow passage tube, creating a gap from the one end. The first component may be formed with an outflow passage or an outflow passage oriented in a direction that intersects the outer circumferential surface of the flow passage tube, and the transmissive member may be arranged such that the exit part faces the opening of the flow passage tube, and the supported part may be sandwiched between the first component and the second component along with a sealing member.

Optional combinations of the aforementioned constituting elements, and implementations of the invention in the form of methods, apparatuses, and systems may also be practiced as additional modes of the present invention.

The invention will now be described by reference to the preferred embodiments. This does not intend to limit the scope of the present invention, but to exemplify the invention.

A description will be given of an embodiment of the present invention with reference to the drawings. In the explanations of the figures, the same elements shall be denoted by the same reference numerals, and duplicative explanations will be omitted appropriately. The configuration described below is by way of example only and does not limit the scope of the present invention.

First Embodiment

FIG. 1 is a cross-sectional view showing a schematic configuration of a fluid sterilization device 10 according to the first embodiment. The fluid sterilization device 10 includes a flow passage tube 14 formed with a processing passage 12 for sterilizing a fluid (liquid) passing through the processing passage 12, a light source 16 for radiating ultraviolet light toward the processing passage 12, and a transmissive member 18 provided between the light source 16 and the processing passage 12 and transmitting the ultraviolet light radiated by the light source 16.

The flow passage tube 14 is a cylindrical straight tube and is provided at one end 20 with an outflow passage 22 extending in a radial direction of the flow passage tube 14 and is provided at another end 24 with an inflow passage 26 extending in a radial direction of the flow passage tube 14. A transmissive member 18 for transmitting the ultraviolet light from the light source 16 is provided at the one end 20.

The light source 16 is provided in a light source chamber 30 isolated from the processing passage 12 by the transmissive member 18. The light source chamber 30 is an area defined by the transmissive member 18 and a bottomed cylindrical member 32. The light source 16 includes a light emitting device 34 and a substrate 36. The light emitting device 34 is a light emitting diode (LED) configured to emit ultraviolet light, and the central wavelength or peak wavelength thereof is included in a range of about 200 nm~350 nm. It is preferable that the light emitting device 34 emit ultraviolet light near a wavelength range of 260 nm~290 nm having a high sterilizing efficiency. Such an ultraviolet LED is exemplified by an aluminum gallium nitride (AlGaN) based LED.

Figure 2:
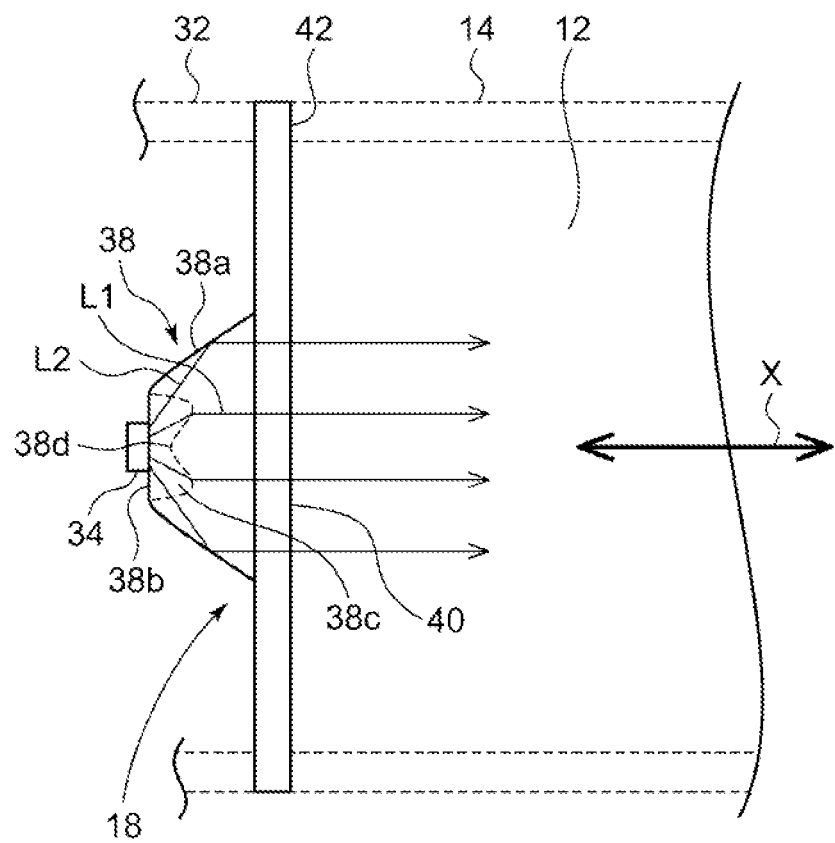
FIG. 2 is a schematic cross-sectional view of the transmissive member.

The transmissive member 18 is a component for sealing an opening of the flow passage tube 14 and focusing the ultraviolet light emitted by the light emitting device 34 toward the processing passage 12. FIG. 2 is a schematic cross-sectional view of the transmissive member 18. FIG. 2 only shows the light emitting device 34 of the light source 16.

As shown in FIG. 2, the transmissive member 18 is a one-piece component including a focusing part 38 that focuses the ultraviolet light L radiated by the light emitting device 34 toward the processing passage by refracting or reflecting the ultraviolet light L, an exit part 40 that guides the ultraviolet light transmitted through the focusing part 38 toward the processing passage 12, and a supported part 42 formed on the outer circumference of the exit part 40 to be contiguous with the exit part 40 and supported by the flow passage tube 14 and the bottomed cylindrical member 32.

The focusing part 38 is a portion shaped in a bowl, and a side surface 38a thereof forms a paraboloidal surface. A recess 38c is formed in a portion of a top part 38b facing the light emitting surface of the light emitting device 34 and a convex lens 38d is formed on the bottom of the recess 38c.

Of the ultraviolet light radiated by the light emitting device 34, the ultraviolet light L1 incident on the convex lens 38d is refracted and exits the exit part 40 before traveling in the processing passage 12 in the longitudinal direction X of the processing passage 12 or in a direction that forms a small angle with respect to the longitudinal direction X. For this reason, the ultraviolet light L1 reaches far into the flow passage tube 14 (toward the other end 24) and improves the efficiency of sterilizing the fluid by ultraviolet light.

Further, of the ultraviolet light radiated by the light emitting device 34, the ultraviolet light L2 directed toward the side surface 38a of the focusing part 38 is reflected inside the side surface 38a and exits the exit part 40 before traveling in the processing passage 12 in the longitudinal direction X of the processing passage 12 or in a direction that forms a small angle with respect to the longitudinal direction X. For this reason, the ultraviolet light L2 reaches far into the flow passage tube 14 (toward the other end 24) and improves the efficiency of sterilizing the fluid by ultraviolet light.

Thus, the ultraviolet light emitted from the light emitting device 34 is directed by the focusing part 38 toward the processing passage 12 so that the amount of ultraviolet light not contributing to sterilization is reduced and the efficiency of sterilizing the fluid is improved. Since the transmissive member 18 is configured as a one-piece component, the only interfaces that the ultraviolet light radiated by the light emitting device 34 passes through before reaching the processing passage 12 are the incident surface and the exit surface of the focusing part 38 so that the reflection occurring at the interfaces is reduced.

Further, the exit part 40 is made of a transparent material such as glass and quartz (refractive index of 1.4~1.8). Still further, the exit part 40 is exposed to the processing passage 12 and is in contact with a liquid, which has a relatively high refractive index (for example, water has a refractive index of about 1.33). Therefore, as compared with the case where the exit part 40 is in contact with air, the refractive index difference at the interface of the exit part 40 is reduced. In other words, the ultraviolet light is not curved significantly in the exit part 40 and reaches far into the flow passage tube 14 (toward the other end 24).

Further, the surface of the exit part 40 is flat as shown in FIG. 2. As mentioned above, the refractive index difference at the interface of the exit part 40 is reduced so that it is not necessary to work the surface (change the light path) from an optical perspective. This simplifies the shape of the transmissive member 18 and reduces the manufacturing cost. It should also be noted that the surface of the exit part 40 forms a part of the inner wall surface of the processing passage 12. Therefore, the flow of the liquid in the processing passage 12 is not blocked seriously by configuring the surface to be flat.

The supported part 42 is a flange having a surface flush with the surface of the exit part 40. In this way, the transmissive member 18 having a flange can be configured in a simple shape.

The transmissive member 18 is a molded component. In this way, mechanical work can be omitted or reduced even if the component has a complicated shape. The transmissive member 18 according to the embodiment is made of synthetic quartz. This reduces degradation of the transmissive member 18 even when the light source radiating ultraviolet light is used.

Second Embodiment

Figure 3:
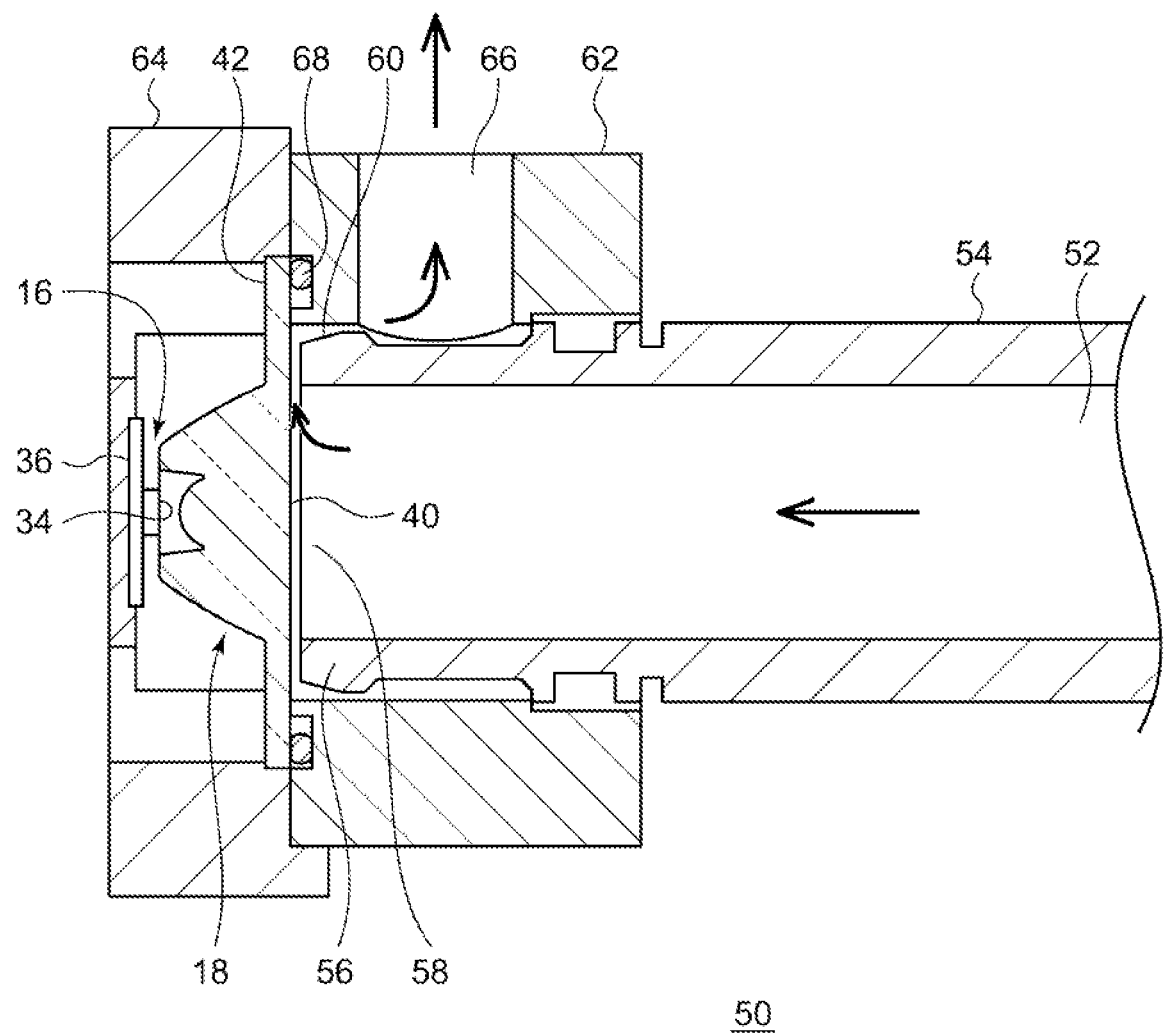
FIG. 3 is a cross-sectional view showing a schematic configuration of a fluid sterilization device according to the second embodiment.
Figure 4:
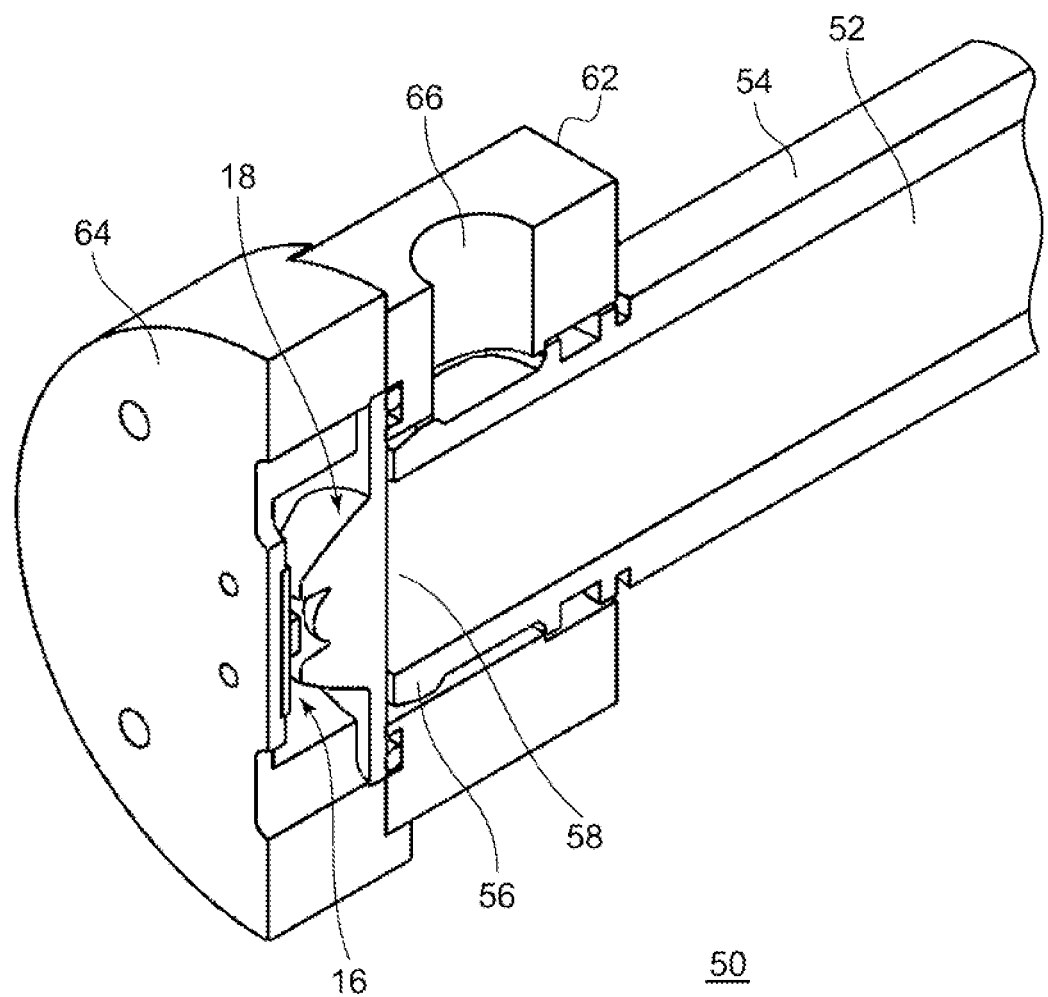
FIG. 4 is a perspective view showing a schematic configuration of the fluid sterilization device according to the second embodiment.

FIG. 3 is a cross-sectional view showing a schematic configuration of a fluid sterilization device 50 according to the second embodiment. FIG. 4 is a perspective view showing a schematic configuration of the fluid sterilization device 50 according to the second embodiment. FIGS. 3 and 4 show only one of the ends of the flow passage tube. The other end of the flow passage tube has a configuration substantially identical to that of the one end so that illustration thereof is omitted. Those components that are equivalent to the components of the first embodiment are denoted with the same reference numerals and a description thereof is omitted as appropriate.

The fluid sterilization device 50 includes a flow passage tube 54 formed with a processing passage 52 for sterilizing a fluid passing through the processing passage 52 and configured as a cylindrical straight tube, the light source 16 for radiating ultraviolet light toward the processing passage 52, and the transmissive member 18 provided between the light source 16 and the processing passage 52 and transmitting the ultraviolet light radiated by the light source 16.

The housing according to this embodiment includes a flow passage tube 54, an annular member 62 as a first component that covers an outer circumferential surface 60 near an opening 58 at one end 56 of the flow passage tube 54, and a bottomed cylindrical member 64 as a second component that covers the opening 58 of the one end 56 of the flow passage tube 54, creating a gap from the one end 56. The annular member 62 is formed with an outflow passage 66 oriented in a direction that intersects the outer circumferential surface 60 of the flow passage tube 54.

As shown in FIG. 3, the fluid flowing in the processing passage 52 of the fluid sterilization device 50 having such a housing passes through the opening 58 of the flow passage tube 54, passes through the gap between the exit part 40 and the one end 56 of the flow passage tube 54, passes through the gap between the outer circumferential surface 60 of the flow passage tube 54 and the inner circumferential surface of the annular member 62, and flows outside from the outflow passage 66.

The transmissive member 18 is arranged such that the exit part 40 faces the opening 58 of the flow passage tube 54. Further, the supported part 42 of the transmissive member 18 is sandwiched between the annular member 62 and the bottomed cylindrical member 64 along with a sealing member 68. The sealing member 68 is preferably made of a material that is not likely to be degraded due to the impact from ultraviolet light. For example, a seal ring of fluoride-containing resin or fluoride-containing rubber is suitable.

Figure 5:
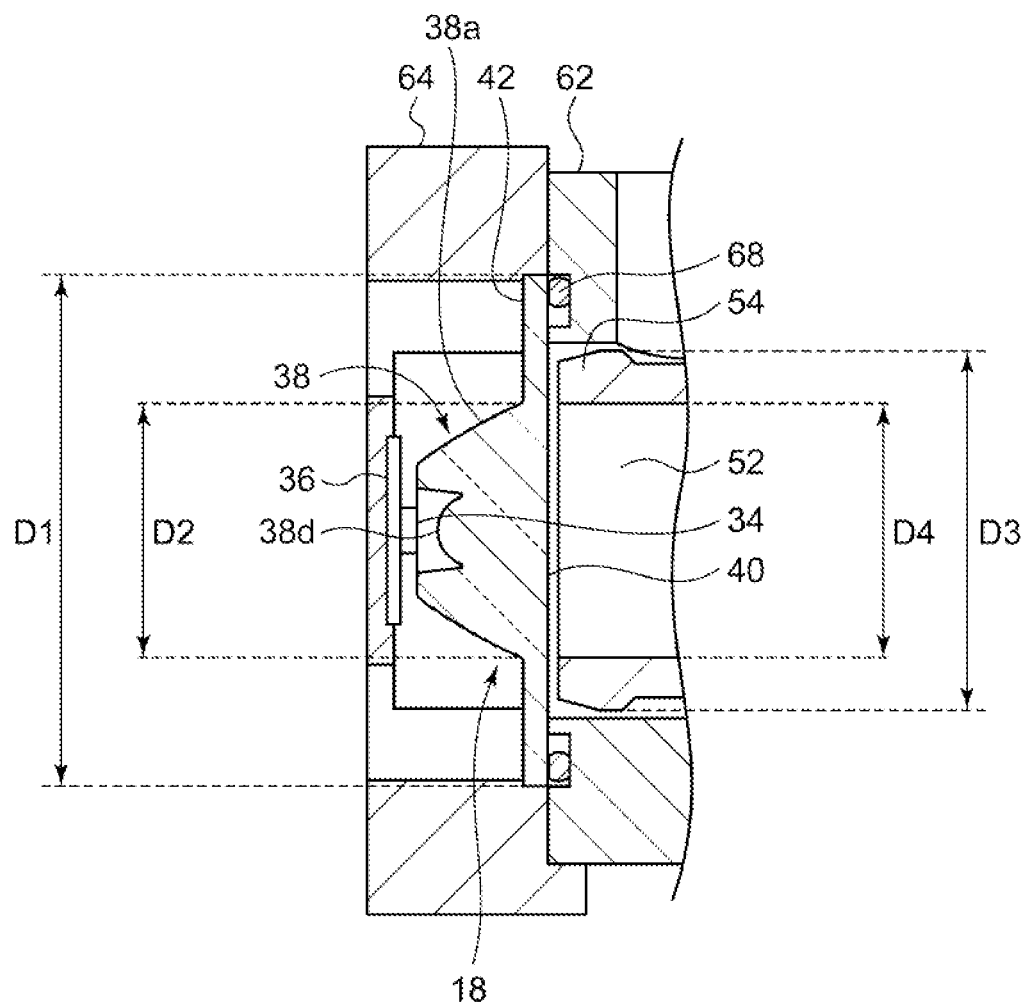
FIG. 5 is an enlarged view of the neighborhood of the transmissive member of FIG. 3.

FIG. 5 is an enlarged view of the neighborhood of the transmissive member 18 of FIG. 3. In the transmissive member 18 of the fluid sterilization device 50 according to this embodiment, the diameter D1 [mm] of the outer edge of the supported part 42 is 1.5 times the maximum diameter D2 of the exit part 40 or larger, or 2.0 times or larger. This ensures that the transmissive member 18 is supported by a housing having a large diameter. The diameter D1 is, for example, 30~100 mm. The maximum diameter D2 is, for example, 10~40 mm. The thickness of the supported part 42 is 1.0~5.0 mm.

The outer diameter D3 [mm] of the flow passage tube 54 is larger than the maximum diameter D2 [mm] of the exit part 40. This ensures that most of the ultraviolet light exiting the exit part 40 is radiated into the processing passage 52. The outer diameter D3 is, for example, 15~70 mm.

Further, the outer diameter D3 [mm] of the flow passage tube 54 is smaller than the diameter D1 [mm] of the outer edge of the supported part 42. This ensures that the transmissive member 18 is supported by the annular member 62 provided on the outer circumference of the flow passage tube 54.

Given that the flow passage tube 54 has an inner diameter D4 [mm] and a length L [mm], L/D4 may be 20 or less. The inner diameter D4 is, for example, 10~40 mm. The length L is, for example, 100~800 mm.

The embodiments of the present invention are not limited to those described above and appropriate combinations or replacements of the features of the embodiments are also encompassed by the present invention. The embodiments may be modified by way of combinations, rearranging of the processing sequence, design changes, etc., based on the knowledge of a skilled person, and such modifications are also within the scope of the present invention.

In the embodiment described above, the light source is provided near the end of the flow passage tube toward the outflow passage. Alternatively, the light source may be provided near the end of the flow passage tube toward the inflow passage. The light source may be provided both near the end of the flow passage tube toward the outflow passage and near the end of the flow passage tube toward the inflow passage.

What is claimed is:
1. A fluid sterilization device comprising:
a housing formed with a processing passage for sterilizing a fluid passing through the processing passage;
a light source that radiates ultraviolet light toward the processing passage; and a transmissive member provided between the light source and the processing passage and transmitting the ultraviolet light radiated by the light source, wherein the transmissive member is a one-piece molded component including:

a focusing part that focuses the ultraviolet light radiated by the light source toward the processing passage by refracting or reflecting the ultraviolet light;

an exit part that guides the ultraviolet light transmitted through the focusing part toward the processing passage, and a supported part formed on an outer circumference of the exit part to be contiguous with the exit part, and supported by the housing, wherein the exit part is exposed to the processing passage.

2. The fluid sterilization device according to claim 1, wherein a surface of the exit part is flat.

3. The fluid sterilization device according to claim 1, wherein the supported part is a flange having a surface flush with a surface of the exit part.

4. The fluid sterilization device according to claim 1, wherein the transmissive member is made of synthetic quartz.

5. The fluid sterilization device according to claim 1, wherein a diameter $D1$ [mm] of an outer edge of the supported part of the transmissive member is 1.5 times a maximum diameter $D2$ [mm] of the exit part or larger.

6. The fluid sterilization device according to claim 1, wherein the housing includes a cylindrical flow passage tube that forms the processing passage, and an outer diameter $D3$ [mm] of the flow passage tube is larger than a maximum diameter $D2$ [mm] of the exit part.

7. The fluid sterilization device according to claim 6, wherein the outer diameter $D3$ [mm] of the flow passage tube is smaller than a diameter $D1$ [mm] of an outer edge of the supported part.

8. The fluid sterilization device according to claim 6, wherein given that the flow passage tube has an inner diameter $D4$ [mm] and a length $L$ [mm], $L/D4$ is 20 or less.

9. The fluid sterilization device according to claim 6, wherein the housing includes:

a first component that covers an outer circumferential surface near an opening of the flow passage tube; and a second component that covers the opening of the flow passage tube, creating a gap from the opening of the flow passage tube, wherein the first component is formed with an outflow passage or an outflow passage oriented in a direction that intersects the outer circumferential surface of the flow passage tube, and the transmissive member is arranged such that the exit part faces the opening of the flow passage tube, and the supported part is sandwiched between the first component and the second component along with a sealing member.

* * * * *